(12) United States Patent
Mihalca

(10) Patent No.: US 7,905,385 B2
(45) Date of Patent: Mar. 15, 2011

(54) JOINING CERAMICS TO METAL

(75) Inventor: Gheorge Mihalca, North Chelmsford, MA (US)

(73) Assignee: Smith & Nephew, Inc., Memphis, TN (US)

(*) Notice: Subject to any disclaimer, the term of this patent is extended or adjusted under 35 U.S.C. 154(b) by 692 days.

(21) Appl. No.: 11/687,908

(22) Filed: Mar. 19, 2007

(65) Prior Publication Data

US 2008/0045991 A1 Feb. 21, 2008

Related U.S. Application Data

(60) Provisional application No. 60/783,363, filed on Mar. 17, 2006.

(51) Int. Cl.
*B23K 31/10* (2006.01)
*B21D 39/04* (2006.01)

(52) U.S. Cl. .................................. 228/122.1; 228/160
(58) Field of Classification Search ................ 428/34.4; 228/122.1, 124.6, 195, 234.1, 160
See application file for complete search history.

(56) References Cited

U.S. PATENT DOCUMENTS

| | | | | |
|---|---|---|---|---|
| 3,023,492 | A * | 3/1962 | Bristow | 428/552 |
| 4,791,935 | A * | 12/1988 | Baudino et al. | 600/333 |
| 6,684,102 | B1 * | 1/2004 | O'Phelan et al. | 607/5 |
| 2002/0179989 | A1 * | 12/2002 | Tatoh et al. | 257/434 |
| 2003/0211386 | A1 * | 11/2003 | Ruth et al. | 429/164 |
| 2004/0099712 | A1 * | 5/2004 | Tonkovich et al. | 228/193 |

\* cited by examiner

*Primary Examiner* — Mark Ruthkosky
*Assistant Examiner* — Erik Kashnikow
(74) *Attorney, Agent, or Firm* — Norman F. Hainer, Jr.

(57) ABSTRACT

The present disclosure relates to methods for joining ceramics to metals and a tool for use in the methods. A medical device and a method of manufacturing a medical device is also disclosed.

24 Claims, 5 Drawing Sheets

JOINING CERAMICS TO METAL

CROSS-REFERENCE TO RELATED APPLICATIONS

This application claims the benefit of U.S. Provisional Application No. 60/783,363, filed Mar. 17, 2006, the disclosure of which is incorporated herein by reference in its entirely.

BACKGROUND

1. Field of the Invention

This present disclosure relates to methods of joining ceramics to metal.

2. Related Art

Some medical devices, e.g., visualization devices, include at least one window of an optical material, for example an ultra-hard, chemically inert monocrystalline material such as sapphire. (Natural and synthetic sapphire will be referred to collectively herein as "sapphire"). The window is joined to a metal wall of the device, typically by first brazing or soldering a metallized portion of the window to a metal housing to form a subassembly, and then welding the metal housing of the subassembly to the metal wall of the device. In some cases, the joint between the sapphire window and the metal housing must survive hundreds of autoclave cycles with uncompromised hermeticity.

Windows are typically formed by slicing a sapphire rod into discs, metallizing the discs (or in some cases metallizing the rod, prior to slicing), and polishing the discs to optical quality while taking care not to affect the metal layer. Before or after brazing the metallized portion each window to the metal housing to form the subassembly, the window may be coated with an antireflection coating.

SUMMARY

In one aspect, the present disclosure features a method that includes brazing a metal member to a surface of a ceramic member to form a brazed part, and slicing the brazed part into portions.

Some implementations include one or more of the following features. The ceramic member comprises sapphire. Each portion includes a portion of the metal member. The method further includes, prior to brazing, metallizing the surface of the ceramic member. The method further includes welding the metal member of one of the portions to a metal housing of a device. The ceramic member is elongated and the metal member extends along the length of the ceramic member. The elongated ceramic member is generally cylindrical. The metal member is in the form of a tube. The method further includes sliding the cylindrical ceramic member into the metal tube prior to brazing. The portions each have a thickness of, e.g., about 1 to 3 mm. The elongated ceramic member is, e.g., at least 10 mm in length. The method can further include polishing the flat surfaces of the portions, and applying an antireflective coating to the polished ceramic.

In another aspect, the present disclosure features a method of manufacturing a medical device including (a) forming subassemblies by (i) brazing a metal member to a surface of a ceramic member to form a brazed part; and (ii) slicing the brazed part to form subassemblies; and (b) welding a subassembly to a metal wall of a respective medical device.

Some implementations may include one or more of the following features. Each subassembly includes a portion of the metal member. The welding step includes placing the subassembly in an opening defined by the metal wall and welding the metal member of the subassembly to a circumferential edge of the opening. The ceramic member is generally cylindrical, and the metal member is in the form of a tube. The method further includes inserting the ceramic member into the metal tube. The method further includes metallizing the surface of the ceramic member prior to brazing. Slicing can be performed so that all of the subassemblies have substantially the same thickness, e.g., about 1 to 3 mm.

In another aspect, the present disclosure features a medical device that includes a metal wall defining an opening, and welded within the opening, a window comprising a ceramic member having a peripheral edge, and a metal ring surrounding the ceramic member and brazed to the peripheral edge thereof.

Some implementations include one or more of the following features. The metal ring has a pair of edges, at least one of which and preferably both of which are substantially flush with broad surfaces of the ceramic member. The metal ring preferably has a wall thickness of less than 0.075", e.g., about 0.030 to 0.060".

The methods described herein generally result in a hermetic joint that is capable of surviving hundreds of autoclave cycles. For example, in some implementations the joint is capable of surviving at least 100 autoclave cycles (sterilization time of 18 min at 275° F. and 31 psig) without leakage. Because brazing is performed prior to slicing, a single brazing operation can be used to form a large number of subassemblies, resulting in significant cost savings and reduction in production time. The geometry of the subassemblies (e.g., the metal surface being flush with the sliced ceramic surface) allows easy manipulation of the subassemblies during subsequent, operations such as polishing and application of an antireflective coating. Antireflective coating, if utilized, is preferably applied after brazing, and thus the antireflective coating need not be formulated to withstand brazing.

A further aspect of the present disclosure includes a tool having a tower plate including at least one through hole and at least one opening, an upper plate located above the lower plate and including at least one through hole and at least, one opening, and at least one guide rod having a first end and a second end, the first end located in the through hole of the lower plate and the second end located in the through hole of the upper plate.

In an embodiment, the tool further includes a metal member having a first end and a second end, the first end located in the opening of the lower plate and the second end located in the opening of the upper plate, the metal member including at least one ceramic member located inside of the metal member. The metal member may include a metallized and nickel plated ceramic member. The metal member may include a plurality of ceramic members (hat are separated by a filler material. The filler material is selected from a group including silver, copper, gold, germanium, and combinations thereof. The metal member, which may include stainless steel, may be in the form of a tube and the ceramic member, which may include sapphire, may be generally cylindrical.

In another embodiment, the lower plate and the upper plate may both include at least two through holes. In a further embodiment, the tool may include at least two guide rods.

Another aspect of the present disclosure includes a method including providing a tool having a lower plate including at least one through hole and at least one opening, an upper plate located above the lower plate and including at least one through hole and at least one opening, and at least one guide rod having a first end and a second end, the first end located in the through hole of the lower plate and the second end located in the through hole of the upper plate, and a metal member having a first end and a second end, the first end located in the opening of the lower plate and the second end located in the opening of the upper plate, the metal member including at least one ceramic member located inside of the metal member; and brazing the metal member to a surface of the ceramic member to form a brazed part.

In an embodiment, the method further includes, prior to brazing, placing the tool in a brazing oven. In another embodiment, the method further includes slicing the brazed part into portions, wherein each portion includes a portion of the metal member.

In yet another embodiment, the metal member includes a plurality of ceramic members separated by a filler material, wherein, the method further includes, prior to brazing, alternately sliding the ceramic members and the filler material into the metal member so that the ceramic members are separated by the filler material.

In a further embodiment, the method further includes, prior to brazing, metallizing the surface of the ceramic member. In yet a further embodiment, the method further includes polishing surfaces of the portions and applying an anti-reflective coating to the polished surfaces. In yet another embodiment, the method further includes welding the metal member of one of the portions to a metal housing of a device.

The details of one or more embodiments of the present disclosure are set forth in the accompanying drawings and the description below. Other features and advantages of the present disclosure will be apparent from the description and drawings, and from the claims.

DESCRIPTION OF DRAWINGS

Further areas of applicability of the present disclosure will become apparent from the detailed description provided hereinafter. It should be understood that the detailed description and specific examples, while indicating the preferred embodiment of the present disclosure, are intended for purposes of illustration only and are not intended to limit the scope of the present disclosure.

BRIEF DESCRIPTION OF THE DRAWINGS

Figure 1:
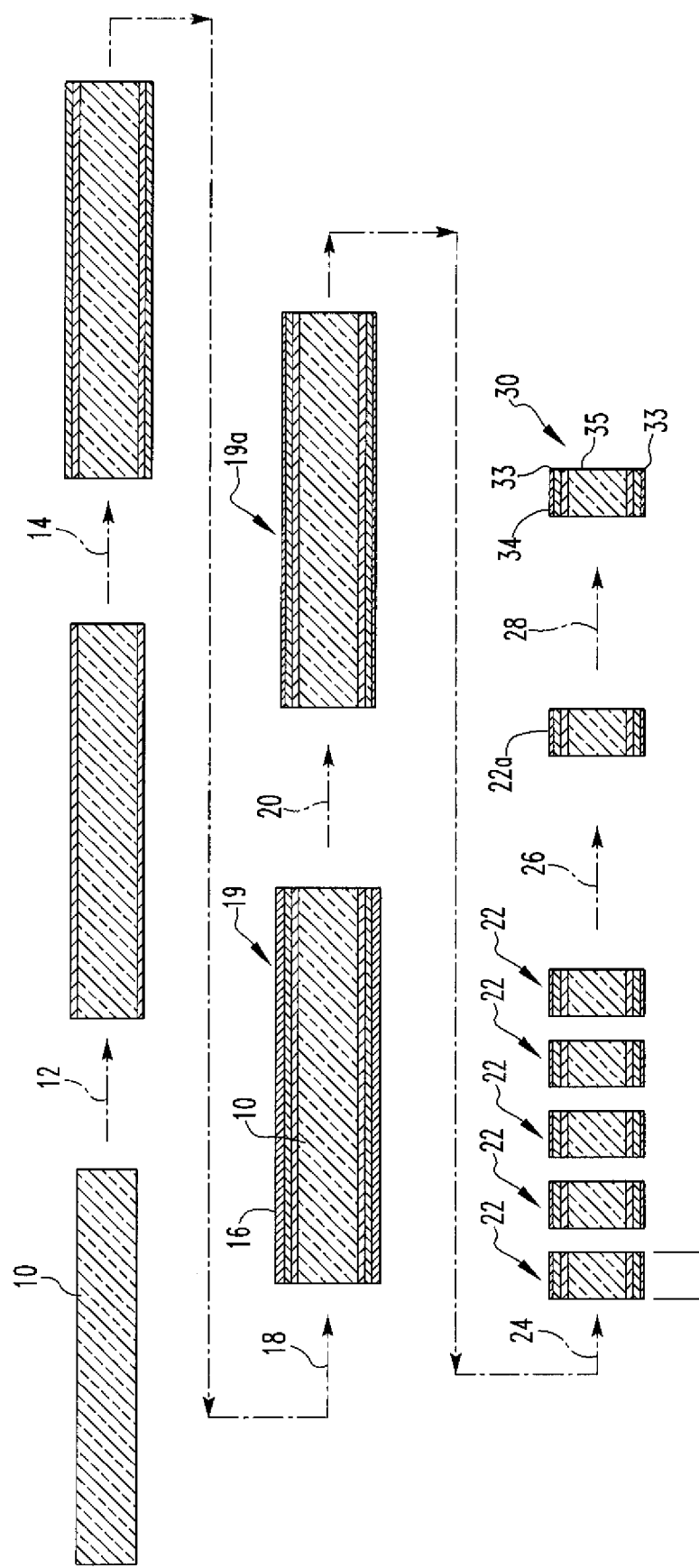

The present disclosure will become more fully understood from the detailed description and the accompanying drawings, wherein:

FIG. 1 is a flow diagram showing steps in a subassembly manufacturing process according to one implementation of the present disclosure.

Figure 2:
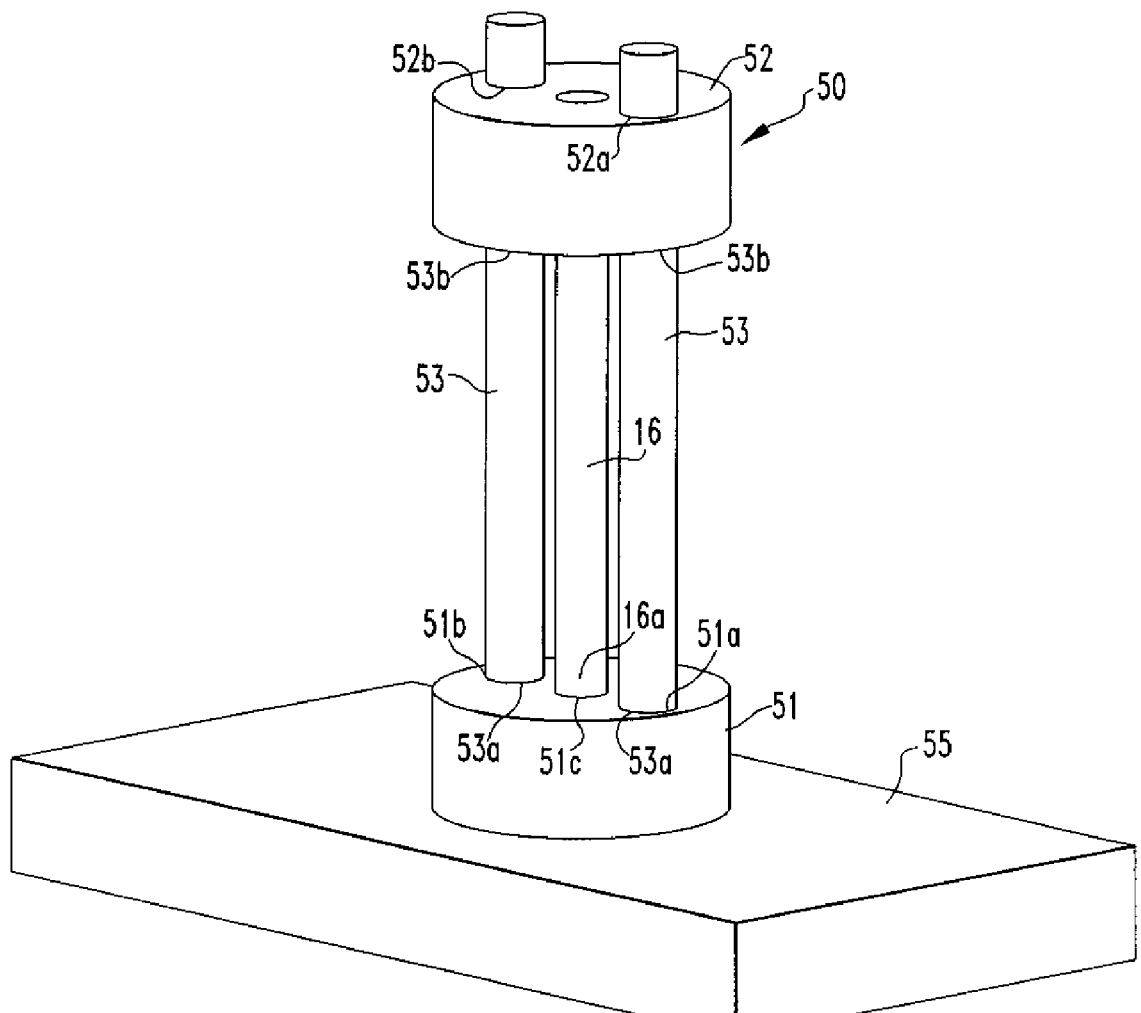

FIG. 2 is a perspective view of a tool of the present disclosure.

Figure 3:
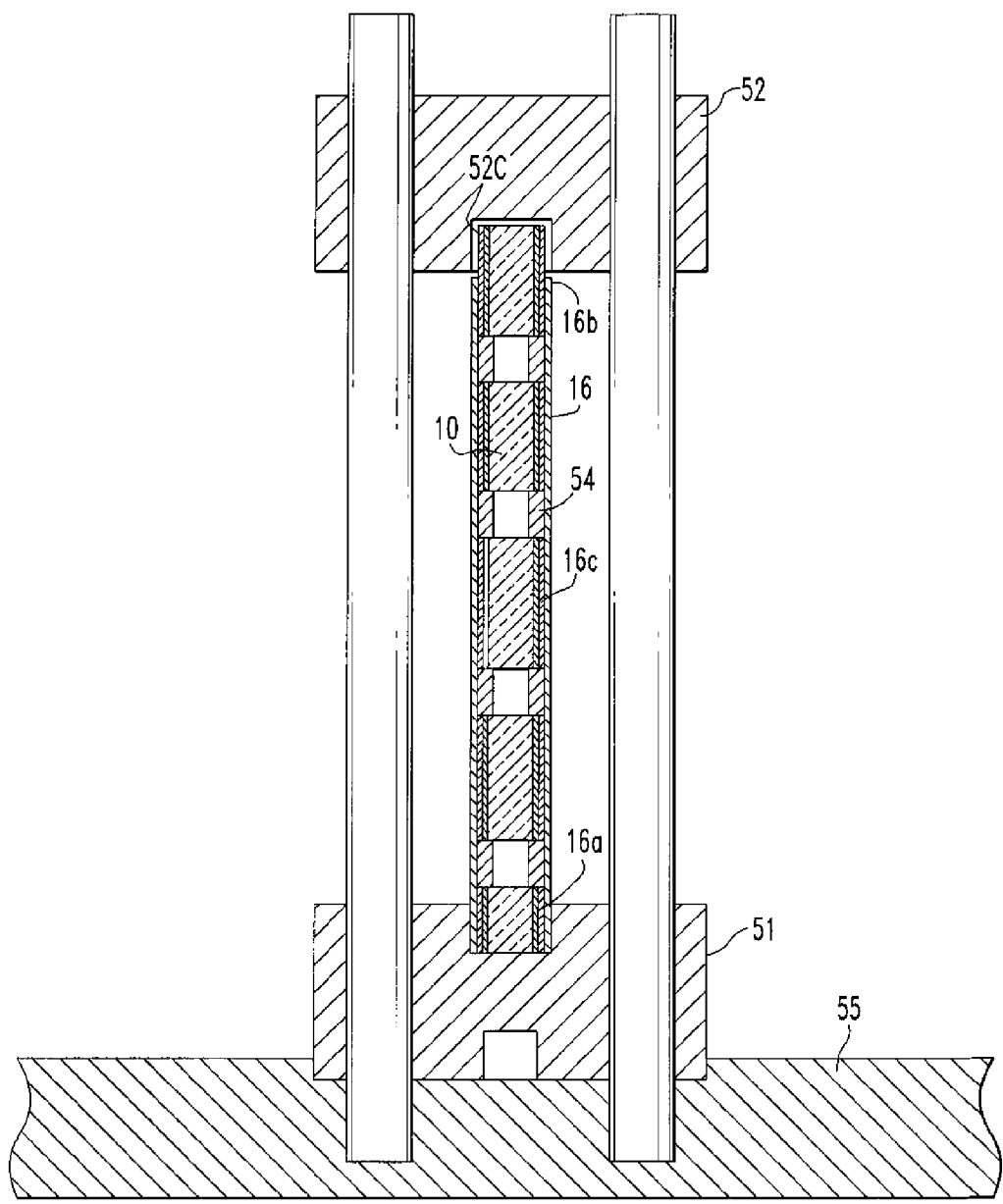

FIG. 3 is a cross-sectional view of the tool of FIG. 2.

Figure 4:
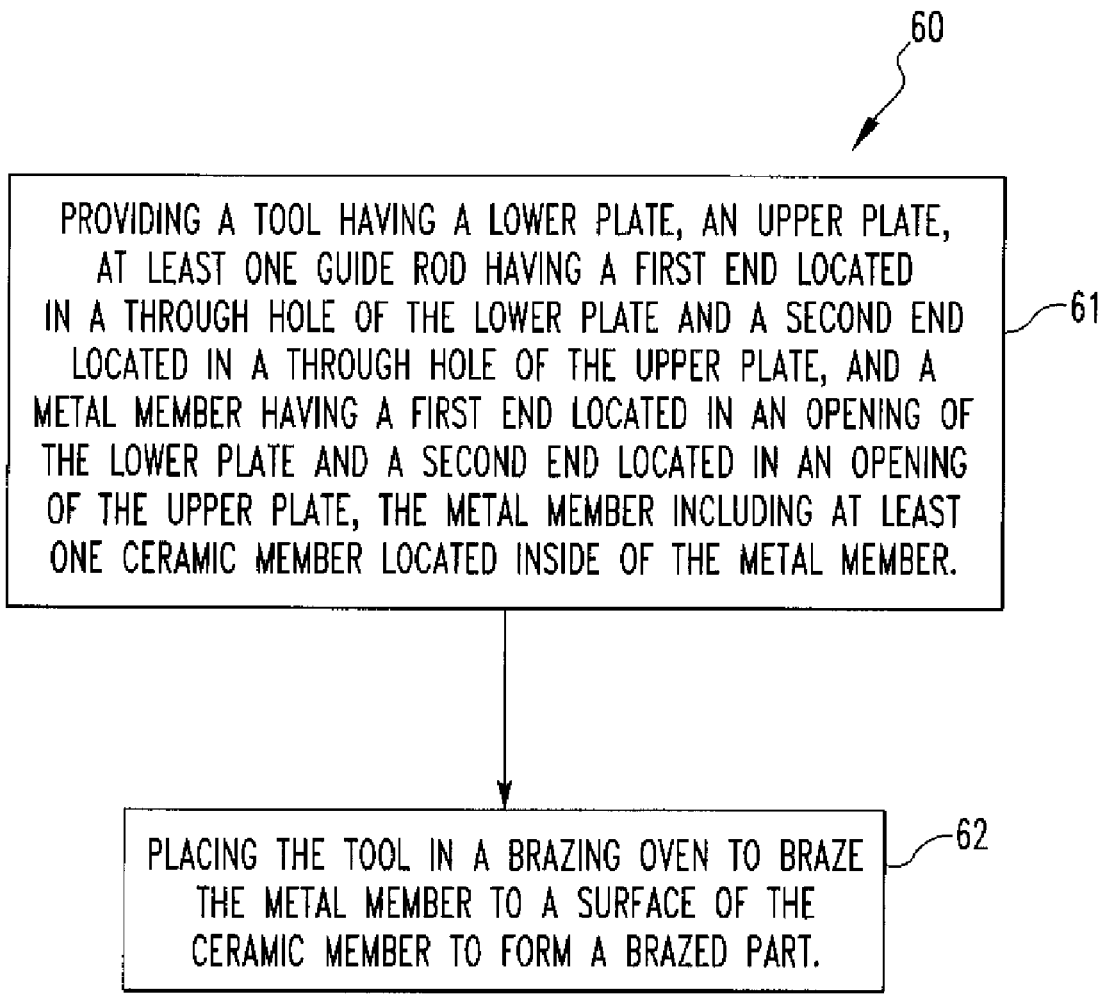

FIG. 4 shows a method of forming a brazed part.

Figure 5:
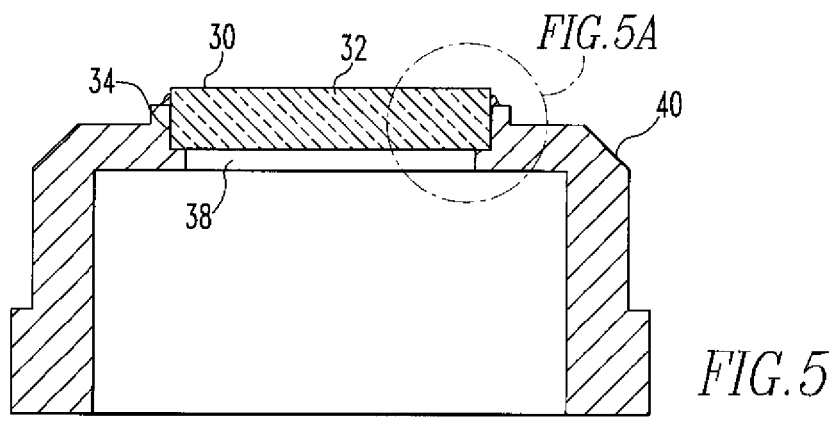

FIG. 5 is a cross-sectional view of a device including a metal housing and a subassembly welded into an opening in the housing.

Figure 5A:
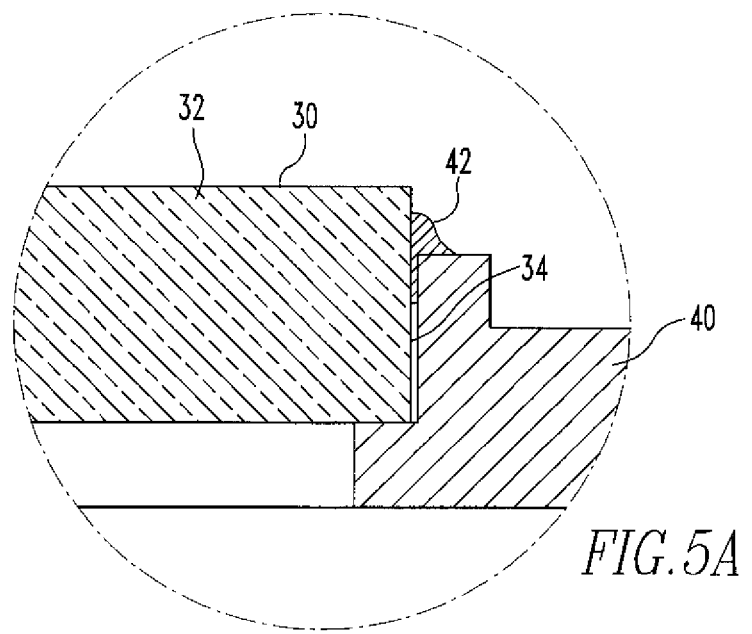

FIG. 5A is an enlarged detail view of the weld in FIG. 5.

Figure 6:
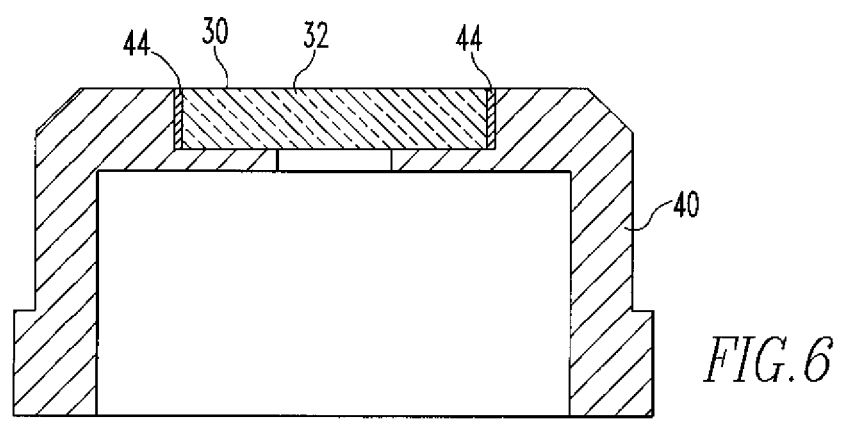

FIG. 6 is a cross-sectional view, similar to FIG. 5, showing an alternative type of weld.

Like reference symbols in the various drawings indicate like elements.

DETAILED DESCRIPTION OF THE PREFERRED EMBODIMENTS

The following description of the preferred embodiment(s) is merely exemplary in nature and is in no way intended to limit the present disclosure, its application, or uses.

A process for a forming a metal/ceramic subassembly includes brazing a metal member to a ceramic member, and then slicing the ceramic member with the metal member brazed to it into portions. The portions can then be subjected to further processing steps to create subassemblies that can be welded to metal devices.

In the process shown in FIG. 1, a ceramic rod 10, which includes sapphire or any other ceramic material known to one of ordinary skill in the art, is first metallized (12) and then plated (14). These two steps facilitate the subsequent brazing of a metal member 16 to the sapphire rod 10 (18). During metallization, a metallizing composition, e.g. a mixture of molybdenum, manganese, tungsten, and other elements such as silica, mixed as a paint, is applied to the sapphire surface and then "fired" in a furnace at temperatures up to 1500° C. -1700° C. The paint reacts with the sapphire (alumina) during the sintering process creating a strong bond. The resulting surface is then nickel plated and sintered again at about 1000° C. Metallization can be omitted if active brazing is used to braze the metal member 16 to the ceramic 10.

Brazing (18) is performed by inserting the sapphire rod 10 into a length of metal tubing 16, and brazing the metal tubing 16 to the metallized and plated sapphire rod 10 to form a brazed part 19 FIG. 2 shows a brazing tool 50 that may be used in brazing the metal tubing 16 to the metallized and plated sapphire rod 10. The tool 50 includes a lower plate 51, an upper plate 52, and two guide rods 53. The lower plate 51 includes a first 51a and a second 51b through hole for the housing of a first end 53a of each guide rod 53. The lower plate 51 also includes an opening 51c for housing a first end 16a of the metal tubing 16. The lower plate 51 acts as a stabilizer for the guide rods 53 and the metal tubing 16. Similar to the lower plate 51, the upper plate 52 includes two through holes 52a-52b and is placed over a second end 53b of each of the guide rods 53, such that the second ends 53b are inserted through the first 52a and second 52b through holes of the upper plate 52. Once the second ends 53b are inserted through the through holes 52a, 52b, a second end (FIG. 3, 16b) of the metal tubing 16 is inserted into the third opening (FIG. 3, 52c) of the upper plate 52. The lower plate 51 may be located on a platform 55 that further stabilizes the tool 50. The guide rods 53, upper 52 and lower 51 plates, and platform, include a metal material or other material that would withstand the temperatures reached during the brazing process, as known to one of ordinary skill in the art. Also, for the purposes of the tool 50, and as can be further evidenced in FIG. 3, the term through hole is defined as a hole that extends throughout the upper and lower plates and the term opening is defined as an opening that does not extend throughout the upper and lower plates, but rather partly through the upper and lower plates wherein the opening is enclosed at one end.

As shown in FIG. 3, the metal tubing 16 includes a plurality of metallized and plated sapphire rods 10 and a filler material 54 between each rod 10. During the brazing process, the upper plate 52 acts as a weight to apply pressure to the second end 16b of the metal tubing 16 and promote up flow of the filler material 54 between the metallized and sapphire plated rod 10 and the inner wall 16c of the metal tubing 16. In this way, the filler material 54 creates a bond between the metallized and plated sapphire rod 10 and the metal tubing 16. In addition, the filler material 54 promotes corrosion resistance of the brazed part 19. The filler material 54 is selected from a group that includes silver, copper, gold, germanium, and combinations thereof.

FIG. 4 shows a method of forming brazed portions 60. The method includes providing the above-mentioned brazing tool 61 and placing the tool in a brazing oven to braze the metal member to a surface of the ceramic member to form a brazed part 62. During the brazing process, the oven is kept at a temperature, and the tool 50 is kept in the oven, for a time sufficient to braze the metallized and sapphire plated rod 10 to the metal tubing 16, as known to one of ordinary skill in the art. As mentioned above, the metal member may include a plurality of ceramic members separated by a filler material. Therefore, the method 60 may further include alternately sliding the ceramic members and the filler material into the metal member so that the ceramic members are separated by the filler material.

Preferably, the clearance between the metal tubing 16 and the rod 10 is very small, and thus it is preferred that the thickness of the metallization and plating layers be very uniform, i.e., that metallization and plating be carefully controlled. The ceramic rod and metal tubing may have any desired length, e.g., at least 10 mm, and in some cases 100 mm or more. Savings in production costs are generally maximized by increasing the length of the rod and tubing as much as possible without deleteriously increasing the clearance between the rod and the tubing to facilitate feeding the rod into the tubing and including the above-mentioned brazing filler material.

The metal tubing 16 can be formed of any desired metal that can be brazed to the metallized and plated sapphire tube and that can be welded to the metal of the device 40 (FIGS. 5 and 5A) to which a formed subassembly 30, discussed further below, is to be joined. For example, if the device 40 is formed of stainless steel, suitable metals for the metal tubing 16 include low carbon stainless steels and iron-based alloys such as Kovar™, which is an iron-based alloy with nickel and cobalt. If the portion of the device 40 containing the subassembly 30 is to be exposed to corrosive materials during use, it is preferred that the metal be corrosion-resistant. The wall of the tubing 16 should generally be thick enough to provide adequate material for welding. In some implementations the tubing 16 is, for example, 0.030 to 0.060" thick. The inner surface of the tubing 16 is generally nickel plated to facilitate brazing. Because nickel plating will tend to interfere with welding, any outer nickel plating is preferably removed prior to slicing, e.g., by the centerless grinding process described below. In some cases, the outer surface is also plated.

If the heat of the brazing operation 18 distorts the metal tubing 16, a centerless grinding operation (20) can be performed to form a brazed part 19*a* having a uniform outer diameter. It is generally important that the outer diameter be substantially uniform so that, the outer diameters of the subassemblies formed from the brazed part are within a relatively small tolerance.

The brazed part 19 or 19*a* is then sliced into a plurality of portions 22 during a slicing operation (24). Preferably, all of the portions have substantially the same thickness (t) e.g., within a tolerance of about ±0.01 mm. A suitable window thickness for use in a medical device is, for example, about 1.5 mm.

Slicing is followed by polishing each portion 22 in a polishing process (26) to form portions 22*a*, and then coating each portion 22*a* in an anti-reflective coating process 28 to form a finished subassembly 30. Each subassembly 30 includes a polished and coated sapphire window 32 and a metal ring 34 (i.e., a slice of the metal tubing 16.) The wall thickness of the ring is relatively low (equal to the thickness of the metal tubing) and the thickness of the ring in the axial direction is substantially equal to the thickness, t, of the sapphire window 32. In other words, as a result of the slicing process the edges 33 of the metal ring 34 are flush with the broad surfaces 35 of the window 32.

The subassembly 30 is incorporated into the device 40 by welding subassembly 30 into an opening 38 in the medical device 40, as shown in FIGS. 5-5A. As shown in FIG. 5A, a weld area 42 is formed during the welding process that firmly joins the subassembly 30 to the metal of the medical device 40. Welding can be performed using laser welding or any desired welding process. The weld may be a corner weld, as shown in FIG. 5A, or a frontal weld 44, as shown diagrammatically in FIG. 6. The device 40 may be, for example, an endoscope, endocoupler, endoscopic video camera, or video-endoscope.

As various modifications could be made to the exemplary embodiments, as described above with reference to the corresponding illustrations, without departing from the scope of the present disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A method comprising:
   brazing a tubular metal member to a surface of an elongated ceramic member to form a brazed part, the tubular member extending along an entire length of the ceramic member and
   slicing the brazed part into portions.

2. The method of claim 1 wherein each portion includes a portion of the metal member.

3. The method of claim 1 further comprising, prior to brazing, metallizing the surface of the ceramic member.

4. The method of claim 1 wherein the ceramic member comprises sapphire.

5. The method of claim 1 further comprising welding the metal member of one of the portions to a metal housing of a device.

6. The method of claim 1 wherein the elongated ceramic member is cylindrical.

7. The method of claim 1 further comprising sliding the cylindrical ceramic member into the metal tube prior to brazing.

8. The method of claim 1 wherein the portions each have a thickness of about 1.5 mm.

9. The method of claim 1 wherein the elongated ceramic member is at least 10 mm in length.

10. The method of claim 1 further comprising polishing surfaces of the portions.

11. The method of claim 10 further comprising applying an antireflective coating to the polished surfaces.

12. A method of manufacturing a medical device comprising
   (a) forming subassemblies by
      (i) brazing a metal member to an entire outer surface of an elongated ceramic member to form a brazed part; and
      (ii) slicing the brazed part to form subassemblies; and
   (b) welding a subassembly to a metal wall of a respective medical device.

13. The method of claim 12 wherein each subassembly includes a portion of the metal member.

14. The method of claim 12 wherein welding comprises placing the subassembly in an opening defined by the metal wall and welding the metal member of the subassembly to a circumferential edge of the opening.

15. The method of claim 12 wherein the elongated ceramic member is cylindrical, and the metal member is in the form of a tube.

16. The method of claim 15 further comprising inserting the ceramic member into the metal tube.

17. The method of claim 12 further comprising metallizing the surface of the ceramic member prior to brazing.

18. The method of claim 12 wherein slicing is performed so that all of the subassemblies have substantially the same thickness.

19. The method of claim 18 wherein the subassemblies have a thickness of about 1.5 mm.

20. The method of claim 12 wherein the brazed part has a length of at least 100 mm.

21. The method of claim 12 wherein the ceramic comprises sapphire.

22. The method of claim 12 further comprising polishing the ceramic of each subassembly.

23. The method of claim 12 further comprising applying an antireflective coating to the polished ceramic.

24. The method of claim 12 wherein welding comprises laser welding.

* * * * *